US006234705B1

(12) United States Patent
Troxell

(10) Patent No.: US 6,234,705 B1
(45) Date of Patent: May 22, 2001

(54) TRANSCONNECTOR FOR COUPLING SPINAL RODS

(75) Inventor: Thomas N. Troxell, Pottstown, PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/286,669

(22) Filed: Apr. 6, 1999

(51) Int. Cl.$^7$ ............... A61B 17/56; F16B 7/06; F16B 7/10

(52) U.S. Cl. ............ 403/237; 403/239; 403/230; 403/248; 403/59; 403/61; 403/112; 403/113; 403/116; 403/117; 606/61; 606/72; 411/353; 411/352; 411/354

(58) Field of Search ............... 606/61, 72; 623/17; 403/59, 61, 112, 113, 116, 117; 411/353, 354, 393, 352, 970, 999, 508, 509, 510

(56) References Cited

U.S. PATENT DOCUMENTS

| | | |
|---|---|---|
| D. 353,003 | 11/1994 | Dinello ............... D24/155 |
| 2,201,087 | 5/1940 | Hallowell ............... 151/37 |
| 4,085,744 | 4/1978 | Lewis et al. ............... 128/69 |
| 4,119,092 * | 10/1978 | Gil ............... 128/92 |
| 4,257,409 | 3/1981 | Bacal et al. ............... 128/69 |
| 4,269,178 | 5/1981 | Keene ............... 128/69 |
| 4,361,141 | 11/1982 | Tanner ............... 128/69 |
| 4,369,770 | 1/1983 | Bacal et al. ............... 128/69 |
| 4,404,967 | 9/1983 | Bacal et al. ............... 128/69 |
| 4,422,451 | 12/1983 | Kalamchi ............... 128/69 |
| 4,433,676 | 2/1984 | Bobechko ............... 128/69 |
| 4,641,636 | 2/1987 | Cotrel ............... 128/69 |
| 4,764,068 | 8/1988 | Crispell ............... 411/393 |
| 4,773,402 | 9/1988 | Asher et al. ............... 128/69 |
| 4,854,795 * | 8/1989 | Duran ............... 411/352 |

(List continued on next page.)

FOREIGN PATENT DOCUMENTS

| | | | |
|---|---|---|---|
| 639264 * | 11/1983 | (CH) | ............... 606/61 |
| 159007 * | 10/1985 | (EP) | ............... 606/61 |
| 303773 * | 2/1989 | (EP) | ............... 606/61 |
| 0 446 092 A1 | 2/1991 | (EP) . | |
| 0 514 303 A1 | 11/1992 | (EP) . | |
| 0 565 149 A2 | 3/1993 | (EP) . | |
| 0 676 177 A2 | 2/1995 | (EP) . | |
| 0 689 799 A1 | 1/1996 | (EP) . | |
| 0 726 064 A2 | 8/1996 | (EP) . | |
| 0 737 448 A1 | 10/1996 | (EP) . | |
| 0 836 836 A2 | 4/1998 | (EP) . | |
| 0 878 170 A2 | 11/1998 | (EP) . | |
| 2 645 427 | 4/1989 | (FR) . | |
| 2 704 137 | 4/1993 | (FR) . | |
| 2 740 673 | 11/1995 | (FR) . | |
| WO 94/08530 | 4/1994 | (WO) . | |
| WO 95/25473 | 9/1995 | (WO) . | |
| WO 97/38640 | 10/1997 | (WO) . | |

*Primary Examiner*—Lynne H. Browne
*Assistant Examiner*—Ernesto Garcia
(74) *Attorney, Agent, or Firm*—Pennie & Edmonds, LLP

(57) ABSTRACT

The present invention is directed to a transconnector for coupling first and second spinal fixation rods or other elongate fixation elements. The transconnector includes a male member, a female member, and a locking member. The male member has a body with a linking element (such as a hook) associated with the lateral end for receiving one of the fixation elements, and a projection extending from the medial end. The female member has a body with a linking element associated with the lateral end for receiving the other fixation element, and a cavity with an opening on the medial end for receiving a portion of the male member projection. The locking member adjustably and rotatably secures the male member projection portion in the cavity in order to accommodate different orientations and separation distances between the first and second fixation elements. The male member may be made as a two component assembly in which the two components can rotate relative to one another for accommodating rod convergence or divergence.

18 Claims, 5 Drawing Sheets

U.S. PATENT DOCUMENTS

| | | | |
|---|---|---|---|
| 5,005,562 | 4/1991 | Cotrel | 128/69 |
| 5,010,879 | 4/1991 | Moriya et al. | 128/69 |
| 5,053,034 | 10/1991 | Olerud | 606/61 |
| 5,084,049 | 1/1992 | Asher et al. | 606/61 |
| 5,102,412 | 4/1992 | Rogozinski | 606/61 |
| 5,129,388 | 7/1992 | Vignaud et al. | 606/61 |
| 5,176,679 | 1/1993 | Lin | 606/61 |
| 5,196,014 | 3/1993 | Lin | 606/61 |
| 5,246,442 | 9/1993 | Ashman et al. | 606/61 |
| 5,254,118 | 10/1993 | Mirkovic | 606/61 |
| 5,261,907 | 11/1993 | Vignaud et al. | 606/60 |
| 5,261,909 | 11/1993 | Sutterlin et al. | 606/61 |
| 5,275,600 | 1/1994 | Allard et al. | 606/61 |
| 5,312,405 | 5/1994 | Korotko et al. | 606/61 |
| 5,330,472 | 7/1994 | Metz-Stavenhagen | 606/53 |
| 5,334,203 | 8/1994 | Wagner | 606/61 |
| 5,360,431 | 11/1994 | Puno et al. | 606/72 |
| 5,395,370 | 3/1995 | Müller et al. | 606/61 |
| 5,397,363 | 3/1995 | Gelbard | 623/17 |
| 5,437,670 | 8/1995 | Sherman et al. | 606/61 |
| 5,439,463 | 8/1995 | Lin | 606/61 |
| 5,454,812 | 10/1995 | Lin | 606/61 |
| 5,487,742 | 1/1996 | Cotrel | 606/61 |
| 5,498,262 | 3/1996 | Bryan | 606/61 |
| 5,498,263 | 3/1996 | DiNello et al. | 606/61 |
| 5,522,816 | 6/1996 | Dinello et al. | 606/61 |
| 5,540,689 | 7/1996 | Sanders et al. | 606/61 |
| 5,549,607 | 8/1996 | Olson et al. | 606/61 |
| 5,569,246 | 10/1996 | Ojima et al. | 606/61 |
| 5,611,800 | 3/1997 | Davis et al. | 606/61 |
| 5,624,442 * | 4/1997 | Mellinger et al. | 606/61 |
| 5,630,816 | 5/1997 | Kambin | 606/61 |
| 5,643,260 | 7/1997 | Doherty | 606/61 |
| 5,643,262 | 7/1997 | Metz-Stavenhagen et al. | 606/61 |
| 5,643,263 | 7/1997 | Simonson | 606/61 |
| 5,662,651 | 9/1997 | Tornier et al. | 606/60 |
| 5,667,507 | 9/1997 | Corin et al. | 606/61 |
| 5,681,312 | 10/1997 | Yuan et al. | 606/61 |
| 5,683,393 | 11/1997 | Ralph | 606/61 |
| 5,688,272 | 11/1997 | Montague et al. | 606/61 |
| 5,693,053 | 12/1997 | Estes | 606/61 |
| 5,697,929 | 12/1997 | Mellinger | 606/61 |
| 5,702,452 | 12/1997 | Argenson et al. | 623/17 |
| 5,707,372 | 1/1998 | Errico et al. | 606/61 |
| 5,709,684 | 1/1998 | Errico et al. | 606/61 |
| 5,709,685 | 1/1998 | Dombrowski et al. | 606/61 |
| 5,716,355 * | 2/1998 | Jackson et al. | 606/61 |
| 5,743,911 | 4/1998 | Cotrel | 606/61 |
| 5,752,955 | 5/1998 | Errico | 606/61 |
| 5,776,198 | 7/1998 | Rabbe et al. | 623/17 |
| 5,800,433 | 9/1998 | Benzel et al. | 606/61 |
| 5,947,966 * | 9/1999 | Drewry et al. | 606/61 |
| 5,980,523 * | 11/1999 | Jackson | 606/61 |

\* cited by examiner

US 6,234,705 B1

TRANSCONNECTOR FOR COUPLING SPINAL RODS

FIELD OF THE INVENTION

The present invention relates to a device for spinal fixation, and in particular to a transconnector for coupling spinal rods, plates, or other elongate members.

BACKGROUND OF THE INVENTION

It is often necessary to surgically treat spinal disorders such as scoliosis. Numerous systems for use in spinal correction and fixation have been disclosed. These systems usually include a pair of elongate members, typically either rods or plates, placed on opposite sides of the vertebral column. Each rod is attached to the spine with various attachment devices. These attachment devices include pedicle screws, plates, spinous process hooks, sublaminar hooks, and pedicle hooks.

It is also well known that the strength and stability of the dual rod assembly can be increased by coupling the two rods with a cross-brace or transconnector which extends substantially horizontal to the longitudinal axes of the rods across the spine. The simplest situation in which a transconnector could be used occurs when the two rods are geometrically aligned. Specifically, the two rods are parallel to each other, i.e. there is no rod convergence or divergence in the medial-lateral direction; the two rods have the same orientation with respect to the coronal plane in the anterior-posterior direction, i.e. the rods are coplanar from a lateral view; and the two rods are located a fixed, predetermined distance from each other.

Due to a wide variety of factors, the two rods are rarely geometrically aligned in clinical situations. There are several ways to address the variations from geometrical alignment. First, one or both of the rods can be bent to accommodate the transconnector. However, any bending in either of the rods can adversely affect the fixation to the spine and comprise clinical outcome. Furthermore, the bending can also adversely affect the mechanical properties of the rods. The transconnector can also be bent so that the disturbance to the rod positioning is minimized. As was the case with bending of the rods, the mechanical properties of the transconnector could be compromised.

Transconnectors with some adjustability have been designed to adapt for variations from geometrical alignment. However, most are multi-piece systems that can be difficult to assemble and use in the surgical environment. Even those that are one-piece designs do not allow for adjustments to compensate for all three modes in which there may be variation from geometrical alignment: convergence or divergence, non-coplanar rods, and variability in rod separation distances.

Thus, there exists a need for an improved transconnector for coupling spinal rods.

SUMMARY OF THE INVENTION

The present invention relates to a transconnector for coupling first and second elongate spinal fixation elements that have different orientations with respect to a plane. The transconnector includes a male member, a female member and a locking member and can be made of any suitable material such as titanium, a titanium alloy, or stainless steel. The male member comprises a body with lateral and medial ends, a linking element associated with the lateral end and being configured and dimensioned to receive one of the fixation elements, and a projection extending from the medial end. The female member comprises a body with lateral and medial ends, a linking element associated with the lateral end and being configured and dimensioned to receive one of the fixation elements, and a cavity with an opening on the medial end which is configured and dimensioned to receive a portion of the male member projection. The locking member adjustably and rotatably secures the male member projection portion in the cavity in order to accommodate different orientations and separation distances between the first and second fixation elements.

In a preferred embodiment, the male member projection is substantially cylindrical and has a pin extending perpendicularly from its longitudinal axis. The pin is slidable in a slot located in a wall of the female member cavity for adjusting the portion of the projection received in the cavity. The slot has a width which is wider than the diameter of the pin so that the projection can rotate in the cavity. In order to further increase the degree of rotation, the side edges of the slot may angle outwardly.

Preferably, the locking member comprises a threaded hole in the body of the female member and a set screw threadably received in the threaded hole. The set screw has a first end for receiving a tool to turn the set screw and a second end contactable with the projection for pressing the projection against the cavity.

The male member body may comprise a link terminal having a lateral end with the male member linking element, an intermediate link having a medial end with the projection of the male member and a lateral end engaging the medial end of the link terminal, and a locking element for securing the link terminal to the intermediate link. Preferably, the medial end of the link terminal includes a first textured surface and the lateral end of the intermediate link includes a second textured surface mating with the first textured surface. The first textured surface is rotatable with respect to the second textured surface for accommodating convergence or divergence between the first and second rods. An example of suitable first and second textured surfaces includes a star-grind pattern.

The locking element preferably comprises a first hole through the medial end of the link terminal, a second hole through the lateral end of the intermediate link aligned with the first hole, and a cap screw insertable in the first and second holes. The cap screw may have a second end with a retaining ring for preventing removal of the cap screw from the first and second holes. The retaining ring may include a resilient member which flexes inward upon insertion of the cap screw through the first and second holes and flexes outward once the resilient member is past a collar in the second hole. Preferably, the resilient member includes an end of the cap screw with a lip and a plurality of slits.

If rods are used for the elongate fixation elements, then the male member linking element preferably comprises a hook and the female member linking element preferably comprises a hook. The lateral ends of the male and female members each may include a threaded hole and a clamping screw threadably received in the respective threaded hole for securing the fixation elements to the respective hook. The fixation elements are preferably clamped between a conical second body portion of the respective clamping screw and a region near the tip portion of the respective hook when the fixation elements are secured to the transconnector.

BRIEF DESCRIPTION OF THE DRAWINGS

Preferred features of the present invention are disclosed in the accompanying drawings, wherein similar reference characters denote similar elements throughout the several views; and wherein.

DETAILED DESCRIPTION OF THE PREFERRED EMBODIMENTS

Figure 1:
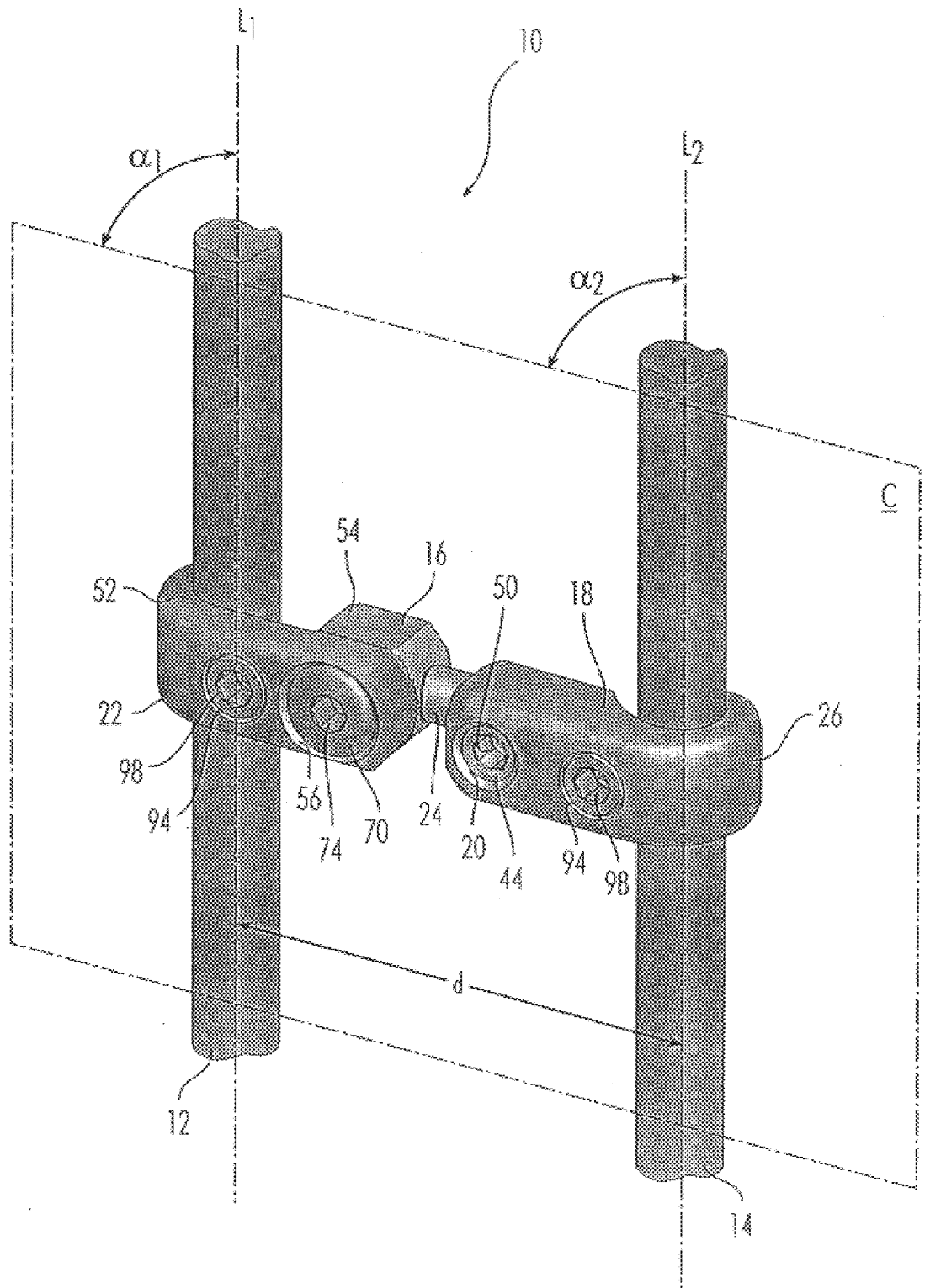
FIG. 1 shows a top perspective view of a transconnector according to the present invention with an elongate fixation element attached at each end.

FIG. 1 shows a transconnector 10 according to the present invention for coupling a first elongate spinal fixation element 12 to a second elongate spinal fixation element 14. Transconnector 10 can be made of any suitable material typically used in orthopaedic applications such as titanium, titanium alloy, or stainless steel. If transconnector 10 is made of a metallic material, preferably it is the same metallic material used for fixation elements 12, 14 to avoid galvanic (mixed-metal) corrosion. First and second fixation elements 12, 14 can be cylindrical rods, rectangular bars, plates, or any other device suitable for spinal fusion. In use, first fixation element 12 extends along one side of the vertebral column and second fixation element 14 extends along the other side of the vertebral column. A wide variety of attachment devices such as hooks, screws, and clamps, can be used to attach first and second fixation elements 12, 14 to the spine.

Transconnector 10 includes a male member 16, a female member 18, and a locking member 20. Male member 16 has a body with a linking element 22 on a lateral end for receiving first fixation element 12 and a projection 24 extending from a medial end of the body. Female member 18 has a body with a linking element 26 on a lateral end for receiving second fixation element 14 and a cavity 28 with an opening 30 (FIG. 5) on a medial end of the body for receiving a portion of projection 24. Locking member 20 secures the portion of projection 24 in cavity 28. The portion of projection 24 received in cavity 28 is adjustable for accommodating different separation distances d between first and second fixation elements 12, 14. This feature allows transconnector 10 to be readily adjusted for different patient anatomies and used in different regions of the spine. For example, the lumbar vertebrae are typically larger than the thoracic vertebrae. As a result, the distance between fixation elements in the lumbar region would be greater than fixation elements in the thoracic region. Because the length of projection that slides into cavity 28 can be changed, transconnector can be adjusted for use in different spinal regions without the need to bend either fixation rods or transconnector 10. In order to further increase the adjustability of transconnector 10, female member 18, cavity 28, and projection 24 can be manufactured in different sizes.

Projection 24 is rotatable in cavity 28 for accommodating differences between the angular orientation of first fixation element 12 with respect to the coronal plane and the angular orientation of second fixation element 14 with respect to the coronal plane. Specifically, first fixation element 12 has a longitudinal axis $L_1$ which runs at an angle $\alpha_1$, with respect to coronal plane C and second fixation element 14 has a longitudinal axis $L_2$ which runs at an angle $\alpha_2$ with respect to coronal plane C, the plane which divides the body in half from front to back. Because projection 24 can rotate in cavity 28, transconnector can be used in situations in which $\alpha_1$, differs from $\alpha_2$ without the need to bend either fixation element or transconnector 10.

Figure 2:
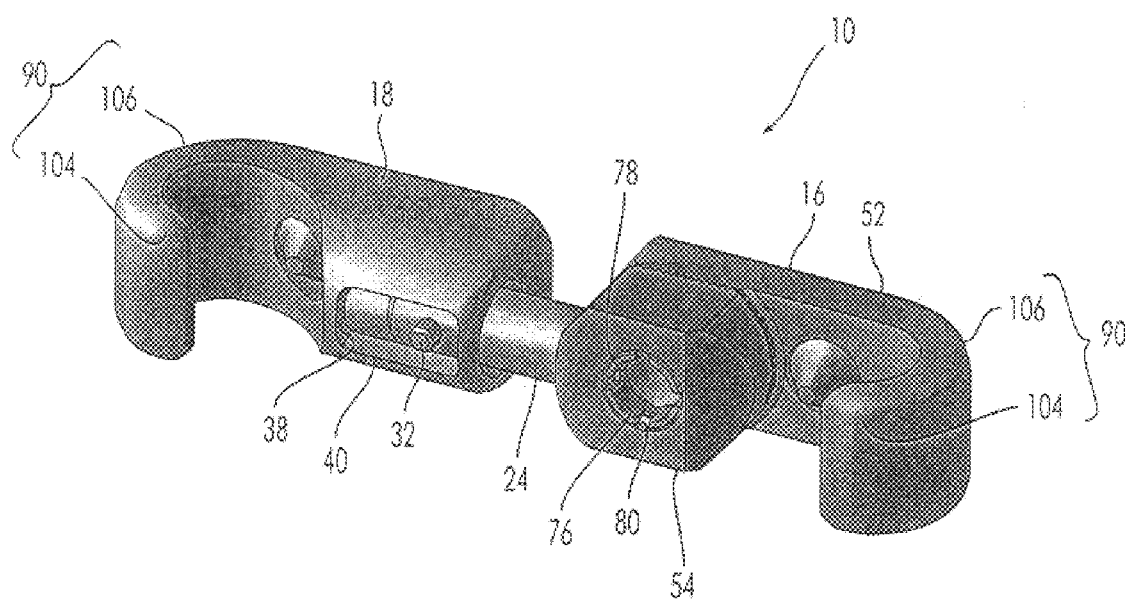
FIG. 2 shows a bottom perspective view of the transconnector without the fixation elements.
Figure 3:
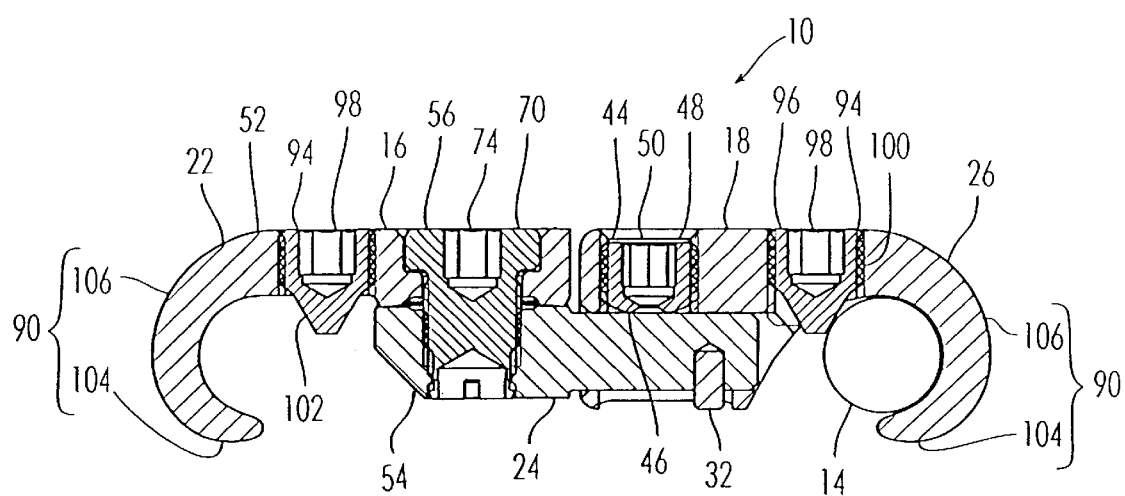
FIG. 3 shows a cross-sectional view of the transconnector with one fixation element attached.
Figure 5:
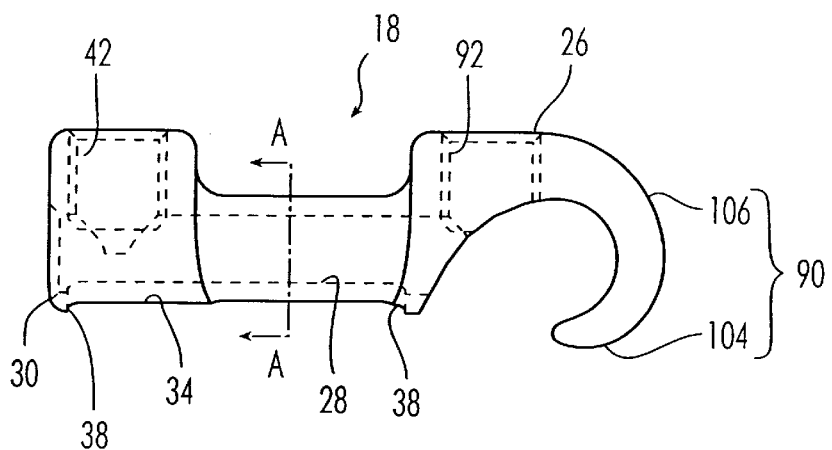
FIG. 5 shows a side view of the female member.
Figure 6:
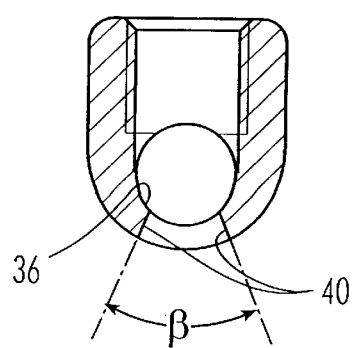
FIG. 6 shows a cross-sectional view of the female member taken along line A—A of FIG. 5.

As seen best in FIGS. 2, 3, and 5, projection 24 is substantially cylindrical and cavity 28 has a corresponding shape to facilitate rotation of projection 24 in cavity 28. Projection 24 has a pin 32 extending perpendicularly therefrom which travels within a slot 34 located on a wall 36 of cavity 28. The engagement of pin 32 with front and back edges 38 limits the length of projection 24 that can slide in cavity 28 and prevents projection 24 from coming completely out of cavity 28. Because the diameter of pin 32 is smaller than the width of slot 34, projection 24 can rotate in cavity 28. The engagement of pin 32 with side edges 40 limits the amount of rotation of projection 24 in cavity 28. Side edges 40 can angle outward to increase the angle of rotation $\beta$ as shown in FIG. 6. A $\beta$ of 45° should be sufficient to accommodate even the most extreme differences between $\alpha_1$, and $\alpha_2$.

As previously noted, locking member 20 secures the portion of projection 24 in cavity 28. FIGS. 1, 3, and 5 show that locking member 20 includes a threaded hole 42 in female member 18 and a set screw 44. Set screw 44 threads into threaded hole and a second end 46 of set screw 44 presses projection 24 to clamp it against the walls of cavity 28. A first end 48 of set screw 44 has an appropriately shaped and sized hole 50 (or a slot) for receiving a surgical instrument like a screwdriver to turn set screw 44.

Figure 7:
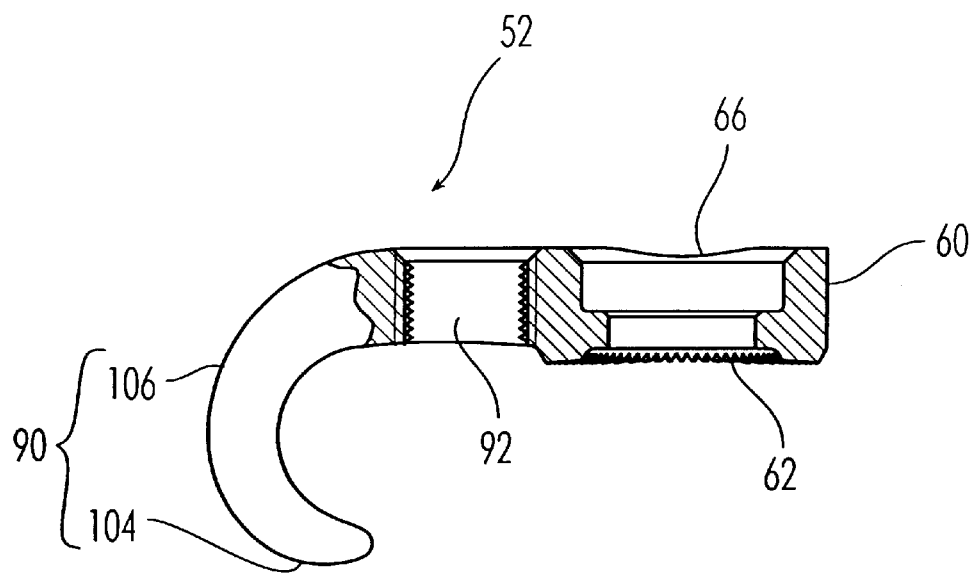
FIG. 7 shows a side view of a link terminal of the male member with portions cut out.
Figure 8:
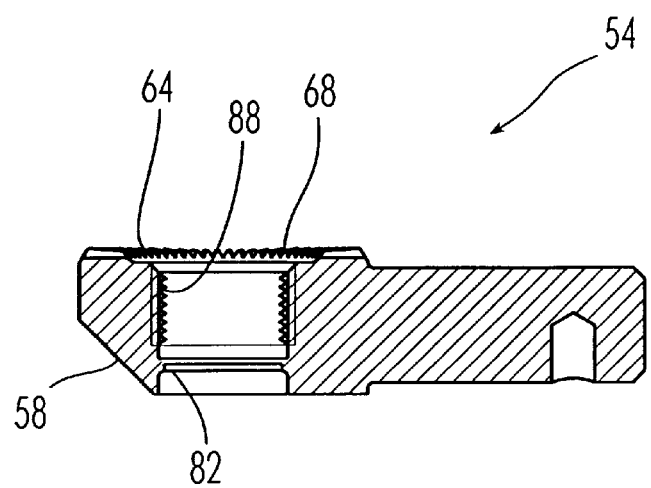
FIG. 8 shows a cross-sectional view of an intermediate link of the male member.

FIGS. 1, 7, and 8 show the body of male member 16 as a two piece assembly which includes a link terminal 52, an intermediate link 54, and a locking element 56 to secure the two together. A lateral end of link terminal 52 has male member linking element 22 and intermediate link 54 has a medial end with projection 24 and a lateral end 58 which engages a medial end 60 of link terminal 52. Medial end 60 of link terminal 52 includes a first textured surface 62 which mates with a second textured surface 64 of lateral end 58 of intermediate link 54 in such a fashion that first textured surface 62 is rotatable with respect to second textured surface 64 to accommodate for any convergence or divergence between first and second fixation elements 12, 14. First and second textured surfaces 62, 64 are provided with a plurality of teeth, such as a star-grind pattern, in order to help maintain link terminal 52 at the desired angular orientation. Locking element 56 includes a first hole 66 through medial end 60 of link terminal 52 and a second hole 68 through lateral end 58. First and second holes 66, 68 align so that a cap screw 70 can be inserted therethrough.

Figure 9:
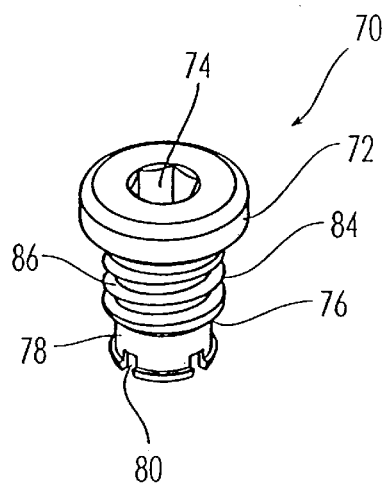
FIG. 9 shows a perspective view of a cap screw used to join the link terminal and intermediate link.
Figure 4:
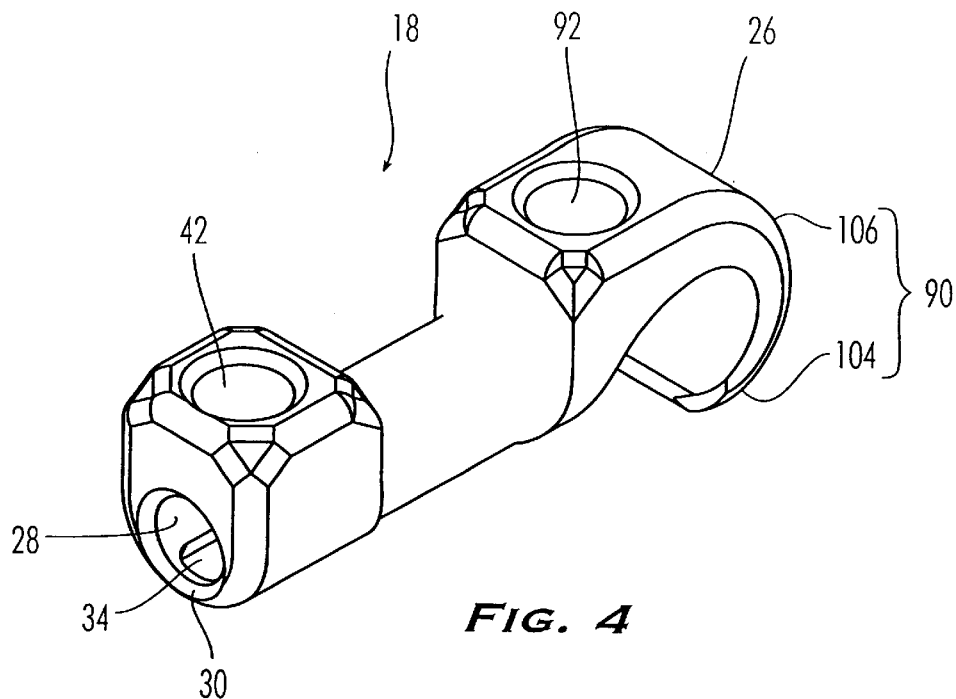
FIG. 4 shows a perspective view of the female member of the transconnector.

Referring to FIG. 9, cap screw 70 has a first end 72 with a slot 74 for receiving a tool to turn cap screw 70 and a second end 76 with a retaining ring 78 for preventing removal of cap screw 70 from first and second holes 66, 68. Retaining ring 78 has slits 80 which allow retaining ring to flex inward to be inserted through a collar 82 in second hole 68. Once retaining ring 78 is inserted past collar 82, retaining ring 78 flexes back outward so that cap screw 70 can not be completely screwed out of first and second holes 66, 68. A body 84 of cap screw 70 is provided with threads 86 which engage threads 88 on the walls of second hole 68.

The structure of linking elements 22, 26 will depend on the structure of fixation elements 12, 14. For example, if fixation rods 12, 14 are elongate plates, then linking elements 22, 26 are configured and dimensioned to receive elongate plates. Such configurations and configurations for other types of fixation elements are well known in the art. If fixation elements 12, 14 are cylindrical rods as shown in the drawings, then linking elements 22, 26 each comprises a hook 90. The lateral ends of male and female members 16, 18 each includes a threaded hole 92 and a clamping screw 94 threadably received in threaded hole 92 for securing first and second fixation elements 12, 14 to hook 90.

As seen best in FIGS. 2 and 3, each clamping screw 94 has a first end 96 with a slot 98 for receiving a tool to turn clamping screw 94, a threaded cylindrical first body portion 100, and a conical second body portion 102. Each hook 90 comprises a tip portion 104 and a curved portion 106. Curved portion 106 has a radius of curvature larger than the radius of fixation elements 12, 14. As a result, the only contact between hooks 90 and fixation elements 12, 14 is at a region near tip portion 104. Furthermore, the only contact between clamping screws 94 and fixation elements 12, 14 is on conical second body portion 102. Thus, fixation elements 12, 14 is clamped between conical second body portion 102 and the region near tip portion 104.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A transconnector for coupling first and second elongate spinal fixation elements that have different orientations, the transconnector comprising:

a male member comprising a link terminal that includes a linking element associated with a lateral end of the link terminal and being configured and dimensioned to receive one of the fixation elements, and a first textured surface on a medial end of the link terminal;

an intermediate link comprising a projection extending from a medial end of the intermediate link and a second textured surface on a lateral end of the intermediate link for mating with the first textured surface such that the first textured surface is rotatable with respect to the second textured surface for accommodating convergence or divergence between the first and second fixation elements, and a locking element for securing the link terminal to the intermediate link;

a female member comprising a body with lateral and medial ends, a linking element associated with the lateral end and being configured and dimensioned to receive one of the fixation elements, and a cavity with an opening on the medial end which is configured and dimensioned to receive a portion of the projection;

a locking member for adjustably and rotatably securing the projection in the cavity in order to accommodate different orientations and separation distances between the first and second fixation elements;

a pin having a diameter and extending perpendicularly from a longitudinal axis of the projection; and a slot located on a wall of the female member cavity, wherein side edges of the slot are configured and dimensioned to angle outwardly and the pin is slideable in the slot for adjusting the portion of the projection received in the cavity and the slot has a width which is wider than the diameter of the pin to allow rotational movement of the pin in the slot and rotation of the projection in the cavity.

2. A transconnector for coupling first and second elongate spinal fixation elements that have different orientations, the transconnector comprising:

a male member comprising a link terminal that includes a linking element associated with a lateral end of the link terminal and being configured and dimensioned to receive one of the fixation elements, and a first textured surface on a medial end of the link terminal;

an intermediate link comprising a substantially cylindrical projection extending from a medial end of the intermediate link and a second textured surface on a lateral end of the intermediate link for mating with the first textured surface such that the first textured surface is rotatable with respect to the second textured surface for accommodating convergence or divergence between the first and second fixation elements and a locking element for securing the link terminal to the intermediate link;

a female member comprising a body with lateral and medial ends, a linking element associated with the lateral end and being configured and dimensioned to receive one of the fixation elements, and a cavity with an opening on the medial end which is configured and dimensioned to receive a portion of the projection;

a locking member for adjustably and rotatably securing the projection in the cavity in order to accommodate different orientations and separation distances between the first and second fixation elements;

a pin having a diameter and extending perpendicularly from a longitudinal axis of the projection; and a slot located on a wall of the female member cavity, wherein side edges of the slot are configured and dimensioned to angle outwardly and the pin is slideable in the slot for adjusting the portion of the projection received in the cavity and the slot has a width which is wider than the diameter of the pin to allow rotational movement of the pin in the slot and rotation of the projection in the cavity.

3. The transconnector of claim 1 wherein the locking member comprises:

a threaded hole in the body of the female member; and a set screw threadably received in the threaded hole and having a first end for receiving a tool to turn the set screw and a second end contactable with the projection for pressing the projection against the cavity.

4. The transconnector of claim 1 wherein the first and second textured surfaces include a star-grind pattern.

5. The transconnector of claim 1 wherein the locking element comprises:

a first hole through the medial end of the link terminal;

a second hole through the lateral end of the intermediate link aligned with the first hole; and a cap screw insertable in the first and second holes.

6. The transconnector of claim 5 wherein the cap screw has a first end for receiving a tool to turn the cap screw and a second end with a retaining ring engaging at least a portion of a collar of the second hole to prevent removal of the cap screw from the first and second holes.

7. The transconnector of claim 6 wherein the cap screw has a body with threads and the second hole is threaded for threadably receiving the cap screw.

8. A transconnector for coupling first and second elongate spinal fixation elements having different orientations, the transconnector comprising:

a male member comprising a link terminal that includes a linking element associated with a lateral end of the link terminal and being configured and dimensioned to receive one of the fixation elements, and a first textured surface on a medial end of the link terminal;

an intermediate link comprising a projection extending from a medial end of the intermediate link and a second textured surface on a lateral end of the intermediate link for mating with the first textured surface such that the first textured surface is rotatable with respect to the second textured surface for accommodating convergence or divergence between the first and second fixation elements and a locking element for securing the link terminal to the intermediate link;

a female member comprising a body with lateral and medial ends, a linking element associated with the lateral end and being configured and dimensioned to receive one of the fixation elements, and a cavity with an opening on the medial end which is configured and dimensioned to receive a portion of the projection; and a locking member for adjustably and rotatably securing the projection in the cavity in order to accommodate different orientations and separation distances between the first and second fixation elements, wherein:

the locking element comprises a first hole through the medial end of the link terminal, a second hole through the lateral end of the intermediate link aligned with the first hole, and a cap screw insertable in the first and second holes and having a first end for receiving a tool to turn the cap screw and a second end with a retaining ring for preventing removal of the cap screw from the first and second holes; and the second hole includes a collar and the retaining ring includes a resilient member, the resilient member flexing inward upon insertion of the cap screw through the first and second holes and flexing outward once the resilient member is past the collar for preventing removal of the cap screw.

9. The transconnector of claim 8 wherein the resilient member includes an end of the cap screw with a lip and a plurality of slits.

10. The transconnector of claim 1 wherein the male member linking element comprises a hook and the female member linking element comprises a hook.

11. The transconnector of claim 10 wherein the lateral end of the male member and the lateral end of the female member each includes a threaded hole and a clamping screw threadably received in the respective threaded hole for securing fixation elements to the respective hooks of the male and female members.

12. The transconnector of claim 11 wherein each clamping screw has a first end for receiving a tool to turn the clamping screw, a threaded cylindrical first body portion, and a conical second body portion.

13. The transconnector of claim 12 wherein the hook of the male member and the hook of the female member each comprises a tip portion and a curved portion having a radius of curvature larger than that of fixation elements.

14. The transconnector of claim 13 in combination with the first and second fixation elements wherein each fixation element is clamped between the conical second body portion of respective each clamping screw and a region near the tip portion of the respective hook.

15. The transconnector of claim 1 wherein the transconnector is made of titanium, a titanium alloy, or stainless steel.

16. The transconnector of claim 8 wherein the projection is substantially cylindrical and the first and second textured surfaces include a star-grind pattern.

17. The transconnector of claim 8 wherein the male member linking element comprises a hook and the female linking element comprises a hook.

18. The transconnector of claim 8 wherein the transconnector is made of titanium, a titanium alloy or stainless.

\* \* \* \* \*